United States Patent
Boyle et al.

(10) Patent No.: US 6,428,777 B1
(45) Date of Patent: Aug. 6, 2002

(54) LOW RESIDUE WATER-CONTAINING ANTIPERSPIRANT STICK

(75) Inventors: Kristin Ann Boyle, Corona del Mar, CA (US); C. Shawn Murphy, Cincinnati, OH (US)

(73) Assignee: Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 10/043,446

(22) Filed: Jan. 10, 2002

(51) Int. Cl.[7] .............................. A61K 7/32; A61K 7/00; A61K 31/74
(52) U.S. Cl. .................. 424/65; 424/78.02; 424/78.08; 424/400; 424/401
(58) Field of Search ................................ 424/65, 78.02, 424/78.08, 400, 401

(56) References Cited

U.S. PATENT DOCUMENTS

| | | |
|---|---|---|
| 4,151,272 A | 4/1979 | Geary et al. |
| 4,526,780 A | 7/1985 | Marschner et al. |
| 4,775,528 A | 10/1988 | Callaghan et al. |
| 5,188,823 A | 2/1993 | Shapiro et al. |
| 5,833,964 A | 11/1998 | Linn et al. |
| 5,843,414 A | 12/1998 | Hilvert et al. |
| 5,955,065 A | 9/1999 | Thong et al. |
| 5,972,319 A | 10/1999 | Linn et al. |
| 6,187,301 B1 | 2/2001 | Scavone et al. |

*Primary Examiner*—Shelley A. Dodson
(74) *Attorney, Agent, or Firm*—Frost Brown Todd LLC

(57) ABSTRACT

Antiperspirant solid stick compositions are disclosed. These compositions do not leave a significant white residue on the skin of the user and exhibit good skin feel when applied. In addition, the compositions allow for the incorporation of free water into the formulation without deactivating the antiperspirant active. The antiperspirant solid stick compositions of the present invention comprise from about 5% to about 35% of a particulate antiperspirant active; from about 10% to about 60% of a volatile solvent; from about 5% to about 30% of a structurant in the form of a wax; from about 0.5% to about 7% of a bentonite and/or hectorite clay; from about 0.2% to about 1.5% of an activator for the clay; and from about 0.5% to about 8% water.

20 Claims, No Drawings

LOW RESIDUE WATER-CONTAINING ANTIPERSPIRANT STICK

TECHNICAL FIELD

The present invention relates to a topical composition which, when applied to the human body, provides an antiperspirant benefit to the user. Particularly, the present invention relates to an antiperspirant composition in solid stick form.

BACKGROUND OF THE INVENTION

Antiperspirant and deodorant products are widely used by people in the world today. Their primary benefit, of course, is their ability to suppress perspiration and/or odors on the body of the user. Since such compositions are generally applied topically to the skin, it is important, when formulating antiperspirant compositions, to make sure that they do not leave an unsightly residue on the skin or clothes (i.e., that they are "non-whitening") and that they provide good skin feel to the user. A product which leaves a white residue on the skin or clothes, or which feels cold, sticky or slimy when applied to the skin may be purchased once, but, will not be re-purchased by the consumer. In the past, delivering a non-whitening product has been accomplished using mechanical processing means for the composition or through the use of butylene glycols in the formulation. The utility of mechanical processing is limited since high shear mixing can only achieve a certain level of non-whitening on the skin. While butylene glycol is effective as a non-whitening agent, it tends to be sticky and tacky to the touch and, therefore, tends to result in undesirable skin feel properties for compositions which incorporate it.

In the past, bentonite or hectorite clays in combination with a polar activator, such as propylene carbonate or ethanol, have been used in roll-on antiperspirant compositions to provide rheological properties and to decrease formula separation. Generally, however, clays were not used in antiperspirant stick formulations. It has now been found that adding clays and activators to an antiperspirant stick has the unexpected result of producing a stick composition which is non-whitening on the skin while at the same time having good skin feel. Currently antiperspirant sticks use butylene glycol or expensive waxes and ethoxylates to achieve a product which is clear on the skin. In addition to being relatively expensive, all of these raw materials have a sticky feel and high drag on the skin. By using a combination of clay and an activator, an antiperspirant stick can achieve non-whitening on the skin, reduced cost, and a smooth skin feel.

Clay and a polar activator can also be used to incorporate water or a water-based extract or additive into an otherwise anhydrous antiperspirant system. In the past, water or water-based extracts or additives have not been incorporated into antiperspirant sticks because they interact negatively with the antiperspirant active. Thus, when water is added to a conventional antiperspirant stick, the water and active form a precipitate which settles out of the anhydrous system, causing both cosmetic and efficacy problems. The present invention permits the use of water in antiperspirant stick compositions, without these problems, through the use of a clay material. The clay and activator can be used to incorporate water or a water-based extract or additive into an anhydrous system because the water can be combined with the clay before the antiperspirant active is added.

U.S. Pat. No. 5,995,065, Thong et al., issued Sep. 21, 1999, relates to topical antiperspirant compositions which incorporate an anhydrous carrier, an aluminum or aluminum/zirconium antiperspirant active, and a water-soluble calcium salt, such as calcium chloride or calcium citrate. The disclosed examples of liquid antiperspirant compositions (Examples 1–5) contain hectorite clay as a thickener or stabilizer. On the other hand, the solid stick examples (Example 9–12) do not include clay materials. This confirms the general approach in the prior art which uses clays primarily as stabilizers or thickeners in liquid or soft antiperspirant compositions, but not in solid stick antiperspirant compositions. See also U.S. Pat. No. 5,188,823, Shapiro, et al., issued Feb. No. 23, 1993, which discloses combinations of clays plus activators in liquid and cream antiperspirant formulations (see Table I).

U.S. Pat. No. 5,833,964, Linn et al., issued Nov. 10, 1998, describes non-whitening antiperspirant sticks which include an antiperspirant active, a gelling agent, a vehicle for the gelling agent, and a mixture of nonvolatile, nonsilicone emollients together with nonvolatile silicone-based emollients both having a refractive index of at least 1.446. Example A discloses an antiperspirant stick composition which includes many conventional solid stick components, but does not include clay or activator components. The patent further teaches (see column 5, lines 43–50) that clay may be used as an inert filler although none of the examples in the patent include clay. See also U.S. Pat. No. 5,972,319, Linn et al., issued Oct. 26, 1999.

U.S. Pat. No. 4,775,528, Callaghan et al., issued Oct. 4, 1988, describes an improved antiperspirant active which comprises a complex of a zirconium hydroxychloride and aluminum chlorhydroxide. Formula II (see column 7) describes an antiperspirant stick composition, which is anhydrous and includes a bentone clay gel. Further, Formula I of the patent discloses a nonaqueous roll-on antiperspirant composition which includes quaternium-18 hectorite clay.

U.S. Pat. No. 5,843,414, Hilvert, et al., issued Dec. 1, 1998, describes antiperspirant compositions in cream (not solid stick) form which are said to have a dry feel on the skin. The compositions include a material selected from bentonite clays, hectorite clays, colloidal silica, talc, microthene, and mixtures thereof.

SUMMARY OF THE INVENTION

The present invention relates to antiperspirant solid stick compositions which comprise:

(a) from about 5% to about 35% of a particulate antiperspirant active;

(b) from about 10% to about 60% of a volatile solvent, such as cyclomethicone D5 (decamethylcyclopentasiloxane);

(c) from about 5% to about 30% of a structurant selected from waxes, and mixtures of waxes having a melting point of at least about 40° C., such as fatty $C_{14}$–$C_{40}$ alcohols, stearyl alcohol, hydrogenated castor oil, hydrogenated vegetable oil, and polyethylene;

(d) from about 0.5% to about 7% of a clay, such as bentonites, hectorites, montmorillonites, colloidal aluminum silicates, and mixtures thereof (such as quaternium-18 hectorite);

(e) from about 0.2% to about 1.5% of an activator for said clay (such as ethanol); and (f) from about 0.5% to about 8% water.

These compositions not only provide effective antiperspirant performance to the user in an aesthetically acceptable solid stick formulation, but also minimize the amount of skin whitening and provide acceptable skin feel to the user. In addition, from a formulational point of view, the antiperspirant sticks of the present invention allow for the incorporation of water or water-based components into an otherwise anhydrous antiperspirant system, without resulting in the deactivation of the antiperspirant active material.

All percents and ratios given herein are "by weight" unless otherwise specified.

All patents and publications noted in this application are incorporated herein by reference.

DETAILED DESCRIPTION OF THE INVENTION

The antiperspirant solid stick compositions of the present invention include a particulate antiperspirant active, a volatile solvent, a structurant, a clay material, a polar activator for the clay, and water, and may optionally contain additional components conventionally found in topical stick-form antiperspirant compositions. Each of those components, as well as the method of making and using the compositions of the present invention, will be discussed in detail below.

As used herein, the term "solid stick" is intended to encompass compositions which typically have penetration force values above about 500 grams, generally above about 1000 grams, as measured at 27° C., 15% relative humidity, using conventional devices, for example a TA-XT2 texture analyzer, manufactured by Texture Technology Corp., Scarsdale, N.Y.

The present composition contains from about 5% to about 35%, preferably from about 15% to about 26%, by weight of a particulate antiperspirant material. These weight percentages are calculated on an anhydrous metal salt basis (exclusive of glycine, the salts of glycine, or other complexing agents). The particulate antiperspirant material preferably has a particle size ranging about 1 to about 100 microns, more preferably from about 1 to about 50 microns. They may be impalpable or microspherical in form and, preferably, have a high bulk density (for example, greater than about 0.7 g/cm$^3$). Any particulate antiperspirant materials known in the art may be used in the present invention. Such materials include, for example, many aluminum or zirconium astringent salts or complexes. Examples of useful antiperspirant materials are described in U.S. Pat. No. 6,287,544, Franklin, et al., issued Sep. 11, 2001; U.S. Pat. No. 6,261,543, Fletcher, et al., issued Jul. 17, 2001; and U.S. Pat. No. 6,187,301, Scavone, et al., issued Feb. 13, 2001, all incorporated herein by reference.

Aluminum salts of this type include aluminum chloride and the aluminum hydroxyhalides having the general formula $Al_2(OH)_xQ_y\cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2−nz is greater than or equal to 0, and B may be selected from the group consisting of halides, nitrate, sulfamate, sulfate, and mixtures thereof. Although only zirconium compounds are exemplified in this context, it will be understood that other Group IV B metal compounds, including hafnium, could be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No 3,792,068, Luedders et al., issued Feb. 12, 1974, incorporated herein by reference, discloses complexes of aluminum, zirconium and amino acids such as glycines. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by:
  (A) co-dissolving in water
    (1) one part $Al_2(OH)_{6-m}Q_m$, wherein Q is an anion selected from the group consisting of chloride, bromide and iodide, and mn is a number from about 0.8 to about 2.0;
    (2) x parts $ZrO(OH)_{2-a}Q_a\cdot nH_2O$, where Q is chloride, bromide or iodide; where a is from about 1 to about 2; where n is from about 1 to about 8; and where x has a value of from about 0.16 to about 1.2;
    (3) p parts neutral amino acid selected from the group consisting of glycine, dl-tryptophane, dl-β-phenylalanine, dl-valine, dl-methionine and β-alanine, and where p has a value of from about 0.06 to about 0.53;
  (B) co-drying the resultant mixture to a friable solid; and
  (C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl\cdot 2H_2O$. Preferred zirconium compounds for preparation of such ZAG-type complexes are zirconyl hydroxychloride having the empirical formula $ZrO(OH)Cl\cdot 3H_2O$ and the zirconyl hydroxyhalides of the empirical formula $ZrO(OH)_{2-a}Cl_2\cdot nH_2O$ wherein a is from about 1.5 to about 1.87, and n is from about 1 to about 7. The preferred amino acid for preparing such ZAG-type complexes is glycine of the formula $CH_2(HN_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the approximate general formula [$Al_2(OH)_4Cl$][$H_2CNH_2$—COOH]. All of these patents are incorporated herein by reference.

Of all the above types of antiperspirant actives, preferred compounds include the 5/6 basic aluminum salts of the empirical formula $AlCL (OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG-type complexes wherein the zirconium salt is $ZrO(OH)Cl.3H_2O$ the aluminum salt is $Al_2(OH)_5Cl2O$ or the aforementioned mixtures of $AlCl_3.6H_2O$ and $Al_2(OH)_5Cl.2H_{22}O$ wherein the total metal to chloride molar ratio in the complex is less than about 1.25, the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

Preferred particulate antiperspirant materials include inorganic or organic salts of aluminum, zirconium or zinc, as well as mixtures of those materials. Aluminum chlorhydrate (ACH) actives and aluminum zirconium tetrachlorohydrex glycine complex are particularly preferred antiperspirant actives for use in the present invention, with the aluminum zirconium tetrachlorohydrex glycine complex being particularly preferred.

Volatile hydrocarbon solvents (such as dodecene) and silicone solvents are well-known for use in cosmetic and deodorant sticks. Volatile silicones known for use in deodorant sticks are preferred for use in the present invention. The volatile silicone material is preferably either a cyclic or a linear polydimethylsiloxane and is present at a level of from about 10% to about 60%, preferably from about 20% to about 50%, of the composition.

The cyclic polydimethylsiloxanes preferably include from about 3 to about 7 silicon atoms, more preferably from about 4 to about 5 silicon atoms. The general formula for such siloxanes is

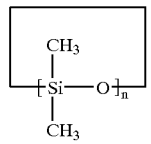

wherein n is from about 3 to about 7. The linear polydimethylsiloxanes contain from about 3 to about 9 silicon atoms and have the general formula $(CH_3)_3Si$—$O[Si(CH_3)_2$—$O]_n$-$Si(CH_3)_3$, wherein n is from about 1 to about 7.

Silicones of the above type are commercially available, for example, from Dow Corning Corporation (Dow Corning 344, 345 and 200 fluids), Union Carbide (Silicone 7207 and Silicone 7158), and Stauffer Chemical (SWS–03314), as well as from General Electric Specialty Chemicals.

The linear volatile silicone materials generally have viscosities of less than about 5 centistokes at 25° C., while the cyclic materials have viscosities less than about 10 centistokes. "Volatile" means that the material has a measurable vapor pressure. A description of volatile silicones is found in Todd and Byers, "Volatile Silicone Fluids for Cosmetics", Cosmetics and Toiletries, 91:27–32 (1976), incorporated herein by reference.

Cyclic polydimethylsiloxanes, and particularly cyclomethicone D-5 (decamethylcyclopentasiloxane) and D-7 (tetradecamethylcycloheptasiloxane), are preferred for use in the compositions of the present invention.

The structurant material is present in the compositions of the present invention at from about 5% to about 30%, preferably from about 12% to about 25%, of the total composition. The structurant materials are materials which are appropriate for topical administration, compatible with the other ingredients in the formulation, and have a melting point of at least about 40° C.; they generally are selected from high melting point and low melting point waxes, and mixtures of those materials (although other well-known materials may be used). Examples of structurant materials useful in the present invention include $C_{14}$–$C_{40}$ fatty alcohols, polyethylene, alkyl ($C_{18}$–$C_{45}$) methyl siloxanes, jojoba ester waxes, hydrogenated vegetable oils, and mixtures thereof. High melting point waxes (65–101° C.) include such materials as beeswax, montan, ozokerite, ceresin, paraffin, hydrogenated castor oil, and $C_{26}$–$C_{50}$ linear alcohols. Low melting point waxes (40–65° C.) include such materials as $C_{14}$–$C_{25}$ fatty alcohols, fatty esters, fatty amides, particularly stearyl alcohol, cetyl alcohol, stearic acid, and polydimethylsiloxanyl beeswax. $C_{16}$–$C_{22}$ fatty alcohols are preferred low melting point waxes. Preferred structurant materials include stearyl alcohol, hydrogenated castor oil, and mixtures of stearyl alcohol and hydrogenated castor oil.

The compositions of the present invention also include a clay component, as well as an activator for the clay. The clays are generally present from about 0.5% to about 7%, preferably from about 1% to about 5%, of the total composition.

Clay materials suitable for use in the compositions of the present invention are selected from the group consisting of montmorillonite clays and hydrophobically treated montmorillonite clays. Montmorillonite clays are those which contain the mineral montmorillonite and are characterized by having a suspending lattice. Examples of these clays include the bentonites, hectorites, and colloidal magnesium aluminum silicates.

Bentonite is colloidal, hydrated aluminum silicate obtained from montmorillonite and has the formula $Al_2O_3.4SiO_2.H_2O$. A more detailed discussion of bentonites can be found in the Kirk-Othmer Encyclopedia of Chemical Technology, $2^{nd}$ Ed., Vol. 3 (1964), pp. 339–360, published by Interscience Publishers, which is incorporated herein by reference.

Hectorite, also a montmorillonite clay, differs from bentonite in that there is almost a complete substitution of aluminum in the lattice structure of bentonite by magnesium. In addition, hectorites contain lithium and fluorine. Barasym NAH-100 is an example of a commercially available synthetic hectorite marketed by NL Industries, Inc.

The magnesium aluminum silicates are complexes of colloidal magnesium aluminum silicate richer in magnesium than aluminum. Magnesium aluminum silicates are commercially available as Veegum (R.T. Vanderbilt Co.).

Examples of clay materials which are preferred for use in the present invention include certain hydrophobically treated montmorillonite clays, e.g., hydrophobic bentonites available under the tradename of "Bentone." Bentone is prepared by reacting bentonite in a cation exchange system with an amine. Different amines are reacted to obtain a variety of Bentones, which may also differ in proportions of $SiO_2$, MgO and $Al_2O_3$. Specific examples of Bentones are Bentone 38, Bentone 34, Bentone 27, Bentone 14, and Bentone LT, all of which have a particle size of below about 5 microns and are commercially available from NL Industries, Inc. (formerly National Lead Company). Bentone 38 is a preferred suspending/thickening agent and is described in greater detail in the Technical Bulletin from the National Lead Company entitled "BENTONE" (incorporated by reference).

An other preferred clay material for use in the present invention is quaternium-18 hectorite.

The activators for the clay are present in the composition of the present invention at from about 0.2% to about 1.5%, preferably from about 0.25% to about 1.25%, of the total composition. The activators are generally polar compounds which chemically activate the clay materials. Examples of such polar activators include propylene carbonate, ethanol, and mixtures of those materials. Ethanol is preferred since it enhances the composition's ability to incorporate water. The clays and activators may be incorporated separately or may be purchased as a mixture of clay, activator and a solvent. For example, Bentone Gel VSSV, commercially available from Element Specialties, is a mixture of about 77% cyclomethicone, 18% quaternium-18 hectorite and 5% SDA-40 alcohol (ethanol).

Although antiperspirant stick compositions typically are anhydrous (i.e., they do not contain free water), since the water tends to negatively interact with the antiperspirant active unless used in a carefully designed formulation, the compositions of the present invention contain from about 0.5% to about 8%, preferably from about 1% to about 5% of water. The presence of the clay in the composition allows the introduction of water without deactivating the antiperspirant active material. The water will typically be added to the composition in the form of a solvent for a water-soluble component, although it may be added as free water as well. Examples of a material which may be added to the compositions of the present invention as water solutions include natural plant extracts, such as ginger extract, which may be added for aesthetic or skin treatment benefits.

The compositions of the present invention may also contain optional components, conventionally used in antiperspirant or deodorant compositions, which modify the physical characteristics of the antiperspirant stick or components of that stick or serve as "active" components when deposited on the skin in addition to the particulate antiperspirant material. Examples of such additional actives include bacteriostats and fungistats. Optional components useful herein are described in the following documents, all incorporated by herein by reference: U.S. Pat. No. 4,049,792, Elsnau, issued Sep. 20, 1977; Canadian Patent 1,164,347, Beckmeyer et al., issued Mar. 27, 1984; European Patent Specification 117,070, May, published Aug. 29, 1984; and Geria, "Formulation of Stick Antiperspirants and Deodorants", Cosmetics and Toiletries, 99:55–60 (1984).

The specific nonactive components that may be used in the present invention will depend upon the characteristics desired for the particular stick compositions. These components would be used at their art-established levels to achieve their art-established benefits. Such components include, for example, emollients, colorants, perfumes, emulsifiers, surfactants, preservatives, and skin feel enhancers. Although the present compositions may also contain fillers and particulate materials (such as talc and silica (fumed and nonfumed)) in addition to the antiperspirant active described above, such particulates may adversely affect the perceived low residue benefits of the present invention and, therefore, their levels should be minimized.

The antiperspirant stick of the present invention may be manufactured using methods known in the art. Typically, all ingredients are combined and heated to a temperature of from about 70° C. to about 85° C. (depending on the type and level of waxes, as well as other components, included in the compositions). The water-containing component is premixed with the activated clay before it is introduced into the composition. The bulk composition is then cooled, with agitation, to a temperature of from about 45° C. to about 65° C., prior to being poured into stick form molds. More specifically, a bentonite gel, a preferred clay material, is formed by mixing a volatile silicone with Bentone and a wetting agent such as propylene carbonate or ethanol, and homogenizing said mixture to form a gel. A bentonite gel may also be purchased as a proprietary product. The bentonite gel and the water-containing component are mixed and heated to a temperature of from about 65° C. to about 70° C. until a homogenous mixture is formed, sequentially mixing and blending the volatile silicone, antiperspirant powder and the oil absorbent powder with said solution to form a stable viscous mixture. Additional suspending agents, thickening agents, stability agents and nonionic emulsifiers may be melted and preblended with the oil absorbent powder or the antiperspirant powder prior to their addition to said Bentone/volatile silicone oil vehicle, or may be preblended and added independently to said Bentone/volatile silicone vehicle or melted and added separately to said viscous vehicle. Perfume and other nonactive components are added to the mixture after cooling to between 55° C. and about 65° C.

The low residue antiperspirant stick compositions of the present invention are used in a conventional manner. Specifically, the compositions may be used to prevent and/or control perspiration wetness by topically applying, one or more times a day, an effective amount of the composition to areas of the body particularly prone to perspiration (for example, the underarm area).

The following nonlimiting examples illustrate the compositions, method of making, and methods of using the present invention described in the present application.

EXAMPLES

Antiperspirant stick compositions of the present invention, having the compositions given in the table below, are formulated using the procedure described above. The compositions are stable, provide good antiperspirant performance with good skin feel and minimized skin whitening, and effectively incorporate the water-containing component.

| Ingredients | Compositions | | | | |
| --- | --- | --- | --- | --- | --- |
| | A % | B % | C % | D % | E % |
| Cyclomethicone | 29.75 | 28.75 | 31.50 | 30.00 | 26.00 |
| Aluminum Zirconium Tetrachlorohydrex Glycine Complex | 24.00 | 24.00 | 24.00 | 24.00 | 24.00 |
| Bentone Gel VS5V | 7.00 | 7.00 | | 7.00 | |
| Quaternium 18 Hectorite | | | 3.00 | | 5.00 |
| SDA-40 Alcohol | | | 0.50 | | 0.75 |
| PPG-14 Butyl Ether | 4.50 | 4.50 | | 6.00 | 5.00 |
| C12–15 Alkyl Benzoate | 11.00 | 11.00 | | | 8.00 |
| Hydrogenated Polydecene | | | 17.00 | 7.00 | |
| Isocetyl Alcohol | | | 2.50 | | |
| Stearyl Alcohol | 15.00 | 15.00 | | | 18.00 |
| Cetyl Alcohol | | | 14.00 | 14.00 | |
| Hydrogenated Castor Oil | 3.25 | 3.25 | | 5.00 | 3.25 |

-continued

| Ingredients | Compositions | | | | |
|---|---|---|---|---|---|
| | A % | B % | C % | D % | E % |
| Propylene Carbonate | | | 1.00 | | 1.50 |
| Aluminum Starch Octenylsuccinate | 2.00 | 2.00 | | | 5.00 |
| Talc | | | 2.00 | 2.00 | |
| Trimethylpentanediol/Adipic Acid/ Isononanoic Acid Copolymer | | 1.50 | 1.50 | 1.50 | |
| Water Soluble Botanical Extract (water solution) | 3.00 | 3.00 | 3.00 | 3.00 | 3.00 |
| Fragrance | 0.50 | 0.50 | 0.50 | 0.50 | 0.50 |

What is claimed is:

1. An antiperspirant solid stick composition comprising:
   (a) from about 5% to about 35% of a particulate antiperspirant active;
   (b) from about 10% to about 60% of a volatile solvent;
   (c) from about 5% to about 30% of a structurant selected from waxes and mixtures of waxes, having a melting point of at least about 40° C;
   (d) from about 0.5% to about 7% of a clay selected from bentonites, hectorites, colloidal aluminum silicates, and mixtures thereof;
   (e) from about 0.2% to about 1.5% of an activator for said clay; and
   (f) from 0.5% to about 8% water.

2. The antiperspirant stick according to claim 1 wherein the antiperspirant active comprises materials selected from organic or inorganic salts of aluminum, zirconium, zinc, and mixtures thereof.

3. The antiperspirant stick according to claim 2 wherein the volatile solvent is selected from cyclic polydimethylsiloxanes containing from about 3 to about 7 silicon atoms, linear polydimethylsiloxanes containing from about 3 to about 9 silicon atoms, and mixtures of those materials.

4. The antiperspirant stick according to claim 3 wherein the structurant is selected from $C_{14}$–$C_{40}$ fatty alcohols, polyethylene, $C_{18}$–$C_{45}$ alkyl methyl siloxanes, jojoba ester waxes, hydrogenated vegetable oils, and mixtures thereof.

5. The antiperspirant stick according to claim 4 wherein the volatile solvent is a cyclic polydimethylsiloxane containing from about 3 to about 7 silicon atoms.

6. The antiperspirant stick according to claim 5 wherein the clay is a hectorite material.

7. The antiperspirant stick according to claim 6 wherein the clay is quaternium-18 hectorite.

8. The antiperspirant stick according to claim 7 wherein the activator is selected from propylene carbonate, ethanol, and mixtures thereof.

9. The antiperspirant stick according to claim 8 wherein the activator is ethanol.

10. The antiperspirant stick according to claim 6 wherein the structurant comprises a material selected from stearyl alcohol, hydrogenated castor oil, and mixtures of stearyl alcohol and hydrogenated castor oil.

11. The antiperspirant stick according to claim 10 wherein the volatile solvent is decamethylcyclopentasiloxane, tetradecamethylcycloheptasiloxane, and mixtures thereof.

12. The antiperspirant stick according to claim 11 wherein the antiperspirant active is an aluminum zirconium chlorohydrex glycine complex.

13. The antiperspirant stick according to claim 12 wherein the clay is quaternium-18 hectorite.

14. The antiperspirant stick according to claim 13 wherein the activator is selected from propylene carbonate, ethanol, and mixtures thereof.

15. The antiperspirant stick according to claim 14 wherein the activator is ethanol.

16. The antiperspirant stick according to claim 15 which contains from about 1% to about 5% water.

17. The antiperspirant stick according to claim 16 which contains from about 15% to about 26% of the antiperspirant active; from about 20% to about 50% of the volatile solvent; and from about 12% to about 25% of the structurant.

18. The antiperspirant stick according to claim 17 which comprises from about 1% to about 5% of the clay component and from about 0.25% to about 1.25% of the activator.

19. The antiperspirant stick according to claim 18 wherein at least a portion of the water component is present in the form of solvent of a water-soluble component.

20. The antiperspirant stick according to claim 19 wherein at least a portion of the water is present in the form of the water solvent for a solution of ginger extract.

* * * * *